United States Patent
Poindexter et al.

[11] Patent Number: 6,096,745
[45] Date of Patent: Aug. 1, 2000

[54] IMIDAZOLONE ANORECTIC AGENTS: III. HETEROARYL DERIVATIVES

[75] Inventors: Graham S. Poindexter, Old Saybrook; Kevin Gillman, Madison, both of Conn.

[73] Assignee: Bristol-Myers Squibb Co., Princeton, N.J.

[21] Appl. No.: 09/261,658

[22] Filed: Mar. 3, 1999

Related U.S. Application Data

[60] Provisional application No. 60/079,359, Mar. 25, 1998.

[51] Int. Cl.$^7$ .................... A61K 31/4166; C07D 233/70; C07D 239/24; C07D 241/10
[52] U.S. Cl. .................... 514/252.05; 514/256; 514/341; 514/380; 514/252.1; 544/333; 544/405; 546/274.1; 546/274.4; 548/260; 548/312.4; 548/314.7; 548/315.1; 548/315.7
[58] Field of Search ...................... 544/333, 405; 546/274.1, 274.4; 548/260, 312.4, 315.7, 315.1, 314.7, 351.1, 351.7; 514/252, 256, 341, 380

[56] References Cited

U.S. PATENT DOCUMENTS 3,894,008   7/1975   Irvine .................................... 546/274.1

OTHER PUBLICATIONS

Gehlert, et al., "Neuropeptide Y Receptor Antagonists in Obesity," *Expert Opinion on Investigational Drugs*, vol. 6, No. 12, Dec. 1997, pp. 1827–1838.

*Primary Examiner*—Mukund J. Shah
*Assistant Examiner*—V. Balasubramanian
*Attorney, Agent, or Firm*—Richard P. Ryan

[57] ABSTRACT

A series of non-peptidergic antagonists of NPY have been synthesized and are comprised of heteroaryl derivatives of imidazolone compounds of Formula 1.

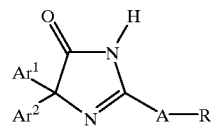

As antagonists of NPY-induced feeding behavior, these compounds and known analogs are expected to act as effective anorexiant agents in promoting weight loss and treating eating disorders.

7 Claims, No Drawings

IMIDAZOLONE ANORECTIC AGENTS: III. HETEROARYL DERIVATIVES

CROSS REFERENCE TO RELATED APPLICATION

This application claims the benefit of U.S. provisional application Ser. No. 60/079,359 filed Mar. 25, 1998.

BACKGROUND OF THE INVENTION

The present invention concerns heterocyclic carbon compounds comprising 2-substituted heteroaryl derivatives of 5,5-diphenyl-3,5-dihydroimidazolones which have been discovered to be NPY antagonists.

2,5,5 (or 2,4,4) -triphenyl-2-imidazolin-4 (or 5)- ones, including analogs wherein the phenyl rings bear an alkyl, alkoxy, or halo substituent, have been described in the chemical literature, generally in connection with chemical process and organic chemical reaction mechanism studies. Also described are 5,5-diphenyl-2-imidazolin-4-ones having a $C_{1-4}$ alkyl substituent in the 2-position of the imidazolinone ring.

Antagonism of neuropeptide Y receptors has been postulated to reduce food consumption in mammals. Several non-peptidic chemotypes have been disclosed in the literature as being antagonists at the $Y_1$ and at the $Y_5$ subtypes of NPY receptors. (See Gehlert and Hipskind, *Exp. Opin. Invest. Drugs*, 1997, 6, pp. 1827–1838.)

Neither applicants' novel 2-substituted heteroaryl derivatives of 5,5-diphenyl-dihydroimidazolones nor the use of these and related dihydroimidazolones for use in treating medical disorders by means of antagonizing NPY receptors following administration of these compounds is known or suggested by prior art.

SUMMARY AND DETAILED DESCRIPTION OF THE INVENTION

The present invention comprises compounds of Formula I, their (I)

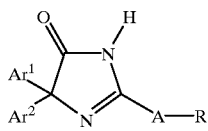

pharmaceutically acceptable acid addition salts and/or their hydrates thereof. In the foregoing structural Formula I, the symbols A, R, $Ar^1$ and $Ar^2$ have the following meanings.

A is a chemical bond or the $C_{1-6}$ alkanyl or $C_{2-6}$ alkenyl group.

R is selected from furan, pyridine, pyrazine, pyrimidine, thiophene, benzotriazole,

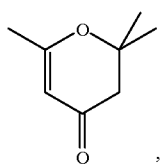

and

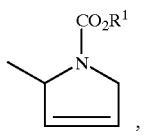

either unsubstituted or substituted with $R^1$ wherein $R^1$ is $C_{1-6}$ alkyl.

$Ar^1$ and $Ar^2$ are independently selected from

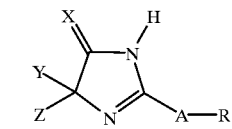

with $R^2$ being hydrogen, halogen, $C_{1-4}$ alkyl or alkoxy.

Preferred compounds are Formula I compounds wherein $Ar^1$ and $Ar^2$ are phenyl rings and R is selected from pyridine and pyrazine.

Another aspect of the invention is the use of structurally related imidazolones to treat medical disorders involved with NPY receptor binding. In this regard, compounds of Formula II are to be administered for treatment of conditions and disorders in which binding at NPY receptors is implicated.

Formula II compounds have the following structural features.

(II)

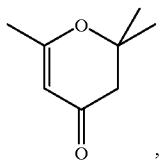

X is selected from oxygen and sulfur.

Y and Z are independently selected from phenyl, optimally substituted phenyl, indole, optimally substituted indole, thienyl, and furanyl.

A is a chemical bond or a $C_{1-6}$ alkanyl or $C_{2-6}$ alkenyl group.

R is selected from furan, pyridine, pyrazine, pyrimidine, thiophene, benzotriazol,

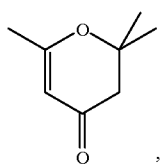

and

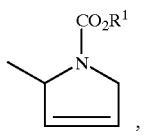

either unsubstituted or substituted with $R^1$ wherein $R^1$ is $C_{1-6}$ alkyl.

As can be seen, Formula II is broader than and encompasses Formula I.

As indicated, the present invention also pertains to pharmaceutically acceptable salts of the Formula I and II compounds. Such salts include those derived from organic and inorganic acids such as, without limitation, hydrochloric, hydrobromic, phosphoric, sulfuric, methanesulfonic, acetic, fumaric, tartaric, moleic, succinic, lactic, citric acid, and the like.

Formula I compounds can be produced by using the processes shown in Scheme 1. The symbols $Ar^1$, $Ar^2$, A and R are as previously defined.

able salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death,

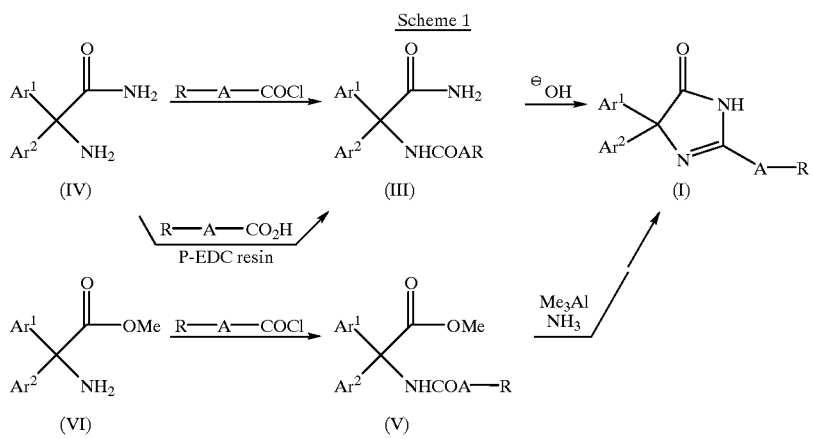

Scheme 1

Unless otherwise indicated in the Specific Embodiments section, known intermediates IV and VI were prepared by standard literature methods. (A typical synthesis of Formula IV compounds is described by Edward, et al., Can. J. Chem., 1967, 45, p.1925. A typical Formula VI compound synthesis is described by Skelly, et al., J. Org. Chem., 1985, 50, p. 267.)

Similar processes employing appropriate modifications can be utilized to provide compounds of Formula II. In addition, synthesis of certain Formula II compounds can be found in the chemical literature. Various reaction intermediates and Formula II products can be prepared by modifications known to one skilled in the art. Additional examples and procedures are provided infra.

The compounds of Formulas I and II demonstrate binding affinity at NPY receptors. The binding interaction has been characterized as antagonism at NPY $Y_5$ receptors. This pharmacologic activity was characterized by using BRI-TN-5BI-4 insect cells infected with NPY $Y_5$-recombinant Baculovirus. These cells which express $Y_5$ receptor were used in a radioligand binding assay employing Iodine-125 labeled PYY ligand. The imidazolones of this invention all showed $IC_{50}$ values of less than 1 $\mu$M.

Formula I and II compounds had good binding affinities as evidenced by $IC_{50}$ values being about 10 $\mu$M or less at NPY $Y_5$ receptors. Preferred compounds have $IC_{50}$ values less than 200 nM.

Pharmacologically, these compounds act as selective NPY antagonists at NPY $Y_5$ receptor sites. As such, the compounds of Formulas I and II are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or II or a pharmaceutically acceptcongestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulemia, and metabolic disorders;

diseases related to sexual dysfunction and reproductive disorders;

conditions or disorders associated with inflammation;

respiratory diseases, such as asthma and conditions related to asthma and bronchoconstriction;

diseases related to abnormal hormone release, such as leutinizing hormone, growth hormone, insulin and prolactin;

sleep disturbance and diabetes.

There is evidence that NPY contributes to certain symptoms in these disorders: hypertension, eating disorders, and depression/anxiety; as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a compound of Formula I or II or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anorectic effects without causing any harmful or untoward side effects. Similarly, the instant compounds can be administered to treat the various diseases, conditions, and disorders listed supra.

Therapeutically, the instant compounds are generally given as pharmaceutical compositions comprised of an effective anorectic amount of a compound of Formula I or II or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyetheleneglycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified.

The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), singlet (s), multiplet (m), doublet (d), triplet (t) doublet of doublets (dd), quartet (q) or pentuplet (p). Abbreviations employed are DMSO-$d_6$, (deuterodimethylsulfoxide), $CDCl_3$ (deuterochloroform), and are otherwise conventional. The infrared (IR) spectral descriptions include only absorption wave numbers ($cm^{-1}$) having functional group identification value. The IR determinations were generally employed using potassium bromide (KBr) as diluent. The elemental analyses are reported as percent by weight. Melting points were obtained using a Thomas Hoover capillary apparatus and are uncorrected. Mass spectra (m/z; $MH^+$) and analytic HPLC (retention time and peak area %) data were obtained.

EXAMPLE 1

General Acylation/Cyclization Procedure for the Preparation of Imidazolones $\alpha$-Amino-$\alpha,\alpha$-diarylacetamide (IV) (0.050 g, 0.22 mmol) was added to a solution of the corresponding carboxylic acid (0.44 mmol), and 0.690 g of P-EDC resin (1.4 meq/g, 0.88 mmol) in 5 mL dry $CH_2Cl_2$. [P-EDC resin was synthesized as described by known literature procedures (e.g., Desai, et al., *Tetrahedron Lett.*, 1993, 48, p. 7685) and is as follows: To a stirred solution of 1-[3-(dimethylamino)propyl]-3- ethylcarbodiimide (13.02 g, 84 mmole) in 50 mL anhydrous N,N-dimethylformamide (DMF) was added chloromethylated polystyrene-divinylbenzene 2% resin (50 g, 70 meq. of Cl; 200–400 mesh, 1.4 meq. Cl/g). After stirring at 100° C. overnight, the mixture was cooled and filtered. The resin was washed (200 mL×3) each with DMF, tetrahydrofuran (THF), and diethyl ether. The resin was then dried in vacuo under reduced pressure providing 60.8 g of P-EDC.]

The reaction mixture was shaken for 36 h at rt, then the crude reaction mixture was filtered and the filter cake was washed with excess $CH_2Cl_2$. The resulting filtrate was evaporated in vacuo to yield a crude solid. This solid was dissolved in 3 mL EtOH and 0.5 mL of 1N NaOH(aq.). The resulting solution was stirred for 16 h then neutralized with 1N HCl(aq). The solvent was evaporated in vacuo and the crude solid was purified by reverse phase HPLC chromatography (YMC Inc., 20×100 mm, 5 μm particle size, 120 Å pore size, C18 stationary phase, ODS-A fast elution: 50–100% (10%MeOH/90%$H_2O$-0.1%TFA):(90%MeOH/10%$H_2O$-0.1%TFA) providing pure imidazolones of Formulas I and II.

Using this procedure with reactants being α-amino-α,α-diphenylacetamide and picolinic acid gave product in Example 2.

EXAMPLE 2

2-(2-Pyridinyl)-3,5-dihydro-5,5-diphenyl-4H-imidazol-4-one

α-Amino-α,α-diphenylacetamide (IV) (0.040 g, 0.18 mmol) was added to a solution of picolinic acid (0.044 g, 0.35 mmol), and 1.0 g of P-EDC resin (0.7 meq/g, 0.707 mmol) in 4 mL dry $CH_2Cl_2$. The reaction mixture was shaken for 24 h at rt, then the crude reaction mixture was filtered and the filter cake was washed with excess $CH_2Cl_2$. The resulting filtrate was evaporated in vacuo to yield a white solid (0.040 g, 50%). This solid was dissolved in 2 mL EtOH and 0.3 mL of 1N NaOH(aq.). The resulting solution was stirred for 12 h then neutralized with 1N HCl(aq.). The solvent was evaporated in vacuo and the crude solid was purified by column chromatography (silica gel/5:1 Hex:Acetone) providing 0.033 g of the title imidazolone (83%) as a white solid. mp 166–167.52 C.; $^1$H NMR ($CDCl_3$, 300 MHz) δ=9.17 (brs,1 H), 8.63 (d, 1 H, J=6.0 Hz), 8.45 (d, 1 H, 9.0 Hz), 7.87 (t, 1 H, J=6.0 Hz), 7.58 (d, 4 H, J=6.0 Hz), 7.46 (m, 1 H), 7.32 (m, 6 H); LRMS m/z (ESI) 314 (M+H)$^+$; Anal. Calcd for $C_{20}H_{15}N_3O \cdot 0.19H_2O$: C, 76.66; H, 4.82; N, 13.41. Found: C, 75.83; H, 4.89; N, 13.26.

Imidazolone products can also be prepared by standard acylation of the appropriate α-amino-α,α-diarylacetamide as described in Example 3.

EXAMPLE 3

2-(3-Pyridinyl)-3,5-dihydro-5,5-diphenyl-4H-imidazol-4-one

α-Amino-α,α-diphenylacetamide (IV) (1.40 g, 6.19 mmol) was added to a solution of triethylamine (2.50 g, 24.8 mmol) and 30 mL dry $CH_2Cl_2$. The solution was cooled to 0° C. and then nicotinoyl chloride hydrochloride (1.43 g, 8.05 mmol) was added in one portion. The reaction was stirred at 0° C. for 1 h then warmed to rt and stirred for a total of 16 h. The reaction was then quenched with 5% $NaHCO_3$ (aq) and the aqueous layer was extracted with $CH_2Cl_2$. The organic fractions were combined, dried with anhydrous $Na_2SO_4$ and evaporated in vacuo to yield a red oil. This oil was chromatograhed (silica gel/4:1 Hex/Acetone) affording the desired intermediate amide as a white solid (1.2 g, 58%). The resulting amide (1.2 g, 3.63 mmol) was dissolved in 30 mL EtOH and 1N NaOH(aq.) (4.0 mL, 4.0 mmol) was added. The reaction was stirred for 2 h at rt, then the reaction was neutralized with 1N HCl(aq). The reaction solvent was evaporated in vacuo and the crude solid was dissolved in $CH_2Cl_2$ and subsequently washed with $H_2O$. The organic phase was dried with anhydrous $Na_2SO_4$ and the solvent was evaporated in vacuo. The resulting solid was purified by column chromatography (silica gel/6:1 Hex:Acetone) producing the title imidazolone as a white solid (0.940 g, 83%). mp 205–206° C.; $^1$H NMR ($CDCl_3$, 300 MHz) δ=9.40 (brs, 1 H), 8.83 (d, 1 H, J=3 Hz), 8.59 (d, 1 H, J=9.0 Hz), 7.56 (d, 4 H, J=6.0 Hz), 7.32 (m, 8 H); LRMS m/z (ESI) 314 (M+H)$^+$; Anal. Calcd for $C_{20}H_{15}N_3O$: C, 76.66; H, 4.82; N, 13.41. Found: C, 76.51; H, 4.83; N, 13.36.

As illustrated in Scheme 1, imidazolone products can also be produced starting from α,α-diarylglycine esters as shown in Example 4.

EXAMPLE 4

2-(4-Pyridinyl)-3,5-dihydro-5,5-diphenyl-4H-imidazol-4-one

α,α-Diphenylglycine methyl ester (IV) (0.300 g, 1.24 mmol) was added to a solution of triethylamine (0.503 g, 4.98 mmol) and 10 mL dry $CH_2Cl_2$. The solution was stirred and then isonicotinoyl chloride hydrochloride (0.441 g, 2.48 mmol) was added in one portion. The reaction was heated and allowed to reflux for a total of 6 h. The reaction was then quenched with 5% $NaHCO_3$(aq) and the aqueous layer was extracted with $CH_2Cl_2$. The organic fractions were combined, dried with anhydrous $Na_2SO_4$ and evaporated in vacuo to yield a yellow foam. This foam was chromatographed (silica gel/4:1 Hex/Acetone) affording the desired intermediate amido ester as a white solid (0.340 g, 79%). The resulting amido ester (0.340 g, 0.983 mmol) was subsequently dissolved in 3 mL dry THF and added dropwise to a solution of saturated $NH_3$(g) in 17 mL dry THF, and 1.08 mL of a 2.0 M solution of $Me_3Al$ in hexanes (2.16 mmol). The reaction was heated to reflux for 16 h under a blanket of nitrogen. The reaction was then cooled to rt and carefully quenched with saturated $NH_4Cl$(aq). The aqueous layer was extracted with EtOAc and the organic phase was dried with anhydrous $Na_2SO_4$ and the solvent was evaporated in vacuo. The resulting solid was purified by column chromatography (silica gel/4:1 Hex:Acetone) producing the title imidazolone as a white solid (0.128 g, 42%). mp 237–238° C.; $^1$H NMR (DMSO-$d_6$, 300 MHz) δ=12.13 (brs, 1 H), 8.82 (d, 2 H, J=6.0 Hz), 8.02 (d, 2 H, J=6.0 Hz), 7.47 (d, 4 H, J=7.2 Hz), 7.37 (m, 6 H); LRMS m/z (ESI) 314 (M+H)$^+$; Anal. Calcd for $C_{20}H_{15}N_3O \cdot 0.5H_2O$: C, 74.52; H, 5.00; N, 13.03. Found: C, 74.52; H, 4.73; N, 12.66.

Using procedures selected from those described supra and making appropriate modifications as would be known to one skilled in synthetic organic chemistry, the following imidazolones were prepared.

EXAMPLE 5

2-[3-(2-Thienyl)propyl]-3,5-dihydro-5,5-diphenyl-4H-imidazol-4-one

This compound was isolated as an off white solid in 5% yield. LRMS m/z (ESI) 361.08 (M+H)$^+$; HPLC ret time 6.66 min.

EXAMPLE 6

2-(2-Pyrazinyl)-3,5-dihydro-5,5-diphenyl-4H-imidazol-4-one

This compound was isolated as an off white solid in 20% yield. LRMS m/z (ESI) 315.3 (M+H)$^+$; HPLC ret time 12.22 min.

EXAMPLE 7

2-(2-Furanyl)-3,5-dihydro-5,5-diphenyl-4H-imidazol-4-one

This compound was isolated as an off white solid in 19% yield. LRMS m/z (ESI) 303.10 (M+H)$^+$; HPLC ret time 4.89 min.

EXAMPLE 8

2-[2-(Furanyl)ethenyl]-3,5-dihydro-5,5-diphenyl-4H-imidazol-4-one

This compound was isolated as an off white solid in 5% yield. LRMS m/z (ESI) 329.13 (M+H)$^+$; HPLC ret time 6.77 min.

EXAMPLE 9

2-(5-Pyrimidinyl)-3,5-dihydro-5,5-diphenyl-4H-imidazol-4-one

This compound was isolated as a white solid in 32% yield. $^1$H NMR (CDCl$_3$) δ 9.41 (s, 3 H), 7.57 (m, 4 H), 7.32 (m, 6 H); $^{13}$C NMR (CDCl$_3$) δ 186.0, 161.1, 155.6, 139.4, 128.8, 128.3, 127.2, 122.9. LRMS m/z(ESI) 315.20 (M+H)$^+$.

EXAMPLE 10

Receptor Binding Assay

Human cDNA of the NPY Y$_5$ receptor was PCR-corrected in Baculovirus which was then used to infect "Hi5" (BTI-TN-5BI-4) insect cells during 48 hr incubation. The cells were harvested and used for the binding assay using iodine-125-labeled-PYY ([$^{125}$I]PYY) as a radioligand. Saturation binding used 0.05–100 nM [$^{125}$I]PYY. Nonspecific binding was determined in the presence of 1000 nM unlabeled PYY and was less than 20% of total binding.

What is claimed is:

1. A compound of Formula I and its pharmaceutically acceptable

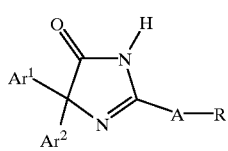

(I)

acid addition salts and/or hydrates thereof, wherein

A is a chemical bond or C$_{1-6}$ alkylene or C$_{2-6}$ alkenylene group;

R is selected from

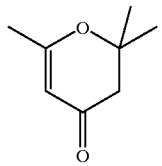

furanyl, pyridinyl, pyrazinyl, pyrimidinyl, thienyl, benzotriazolyl,

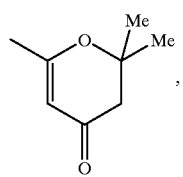

and

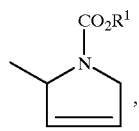

either unsubstituted or substituted with R$^1$ wherein R$^1$ is C$_{1-6}$ alkyl; and Ar$^1$ and Ar$^2$ are independently selected from

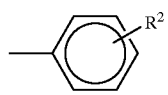

with R$^2$ being hydrogen, halogen, C$_{1-4}$ alkyl or alkoxy.

2. A compound of claim 1 wherein Ar$^1$ and Ar$^2$ are phenyl.

3. A compound of claim 1 wherein A is a chemical bond.

4. A compound of claim 1 wherein R is pyridinyl or pyrazinyl.

5. A compound of claim 3 wherein R is pyridinyl or pyrazinyl.

6. A method of promoting weight loss and treating eating disorders in a mammal comprising administration to a mammalian host of an effective dose of a compound claimed in claim 1.

7. A pharmaceutical composition for use in promoting weight loss and treating eating disorders, the composition comprising an effective amount of a Formula I compound claimed in claim 1 in combination with a pharmaceutically acceptable carrier.

* * * * *

UNITED STATES PATENT AND TRADEMARK OFFICE
CERTIFICATE OF CORRECTION

PATENT NO. : 6,096,745
DATED : August 1, 2000
INVENTOR(S) : Poindexter, et al.

It is certified that error appears in the above-identified patent and that said Letters Patent is hereby corrected as shown below:

Column 10
Line 5, please delete 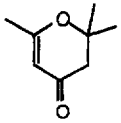

Signed and Sealed this

Fourteenth Day of August, 2001

Attest:

NICHOLAS P. GODICI
Attesting Officer     Acting Director of the United States Patent and Trademark Office